US006899689B1

(12) United States Patent
Modglin (10) Patent No.: US 6,899,689 B1
(45) Date of Patent: May 31, 2005

(54) SPINAL BRACE (75) Inventor: Michael D. Modglin, Braselton, GA (US)

(73) Assignee: DeRoyal Industries, Inc., Powell, TN (US)

(*) Notice: Subject to any disclaimer, the term of this patent is extended or adjusted under 35 U.S.C. 154(b) by 41 days.

(21) Appl. No.: 10/395,763

(22) Filed: Mar. 21, 2003

(51) Int. Cl.$^7$ ............................................... A61F 5/00
(52) U.S. Cl. .............................. 602/19; 602/5; 128/869
(58) Field of Search ............................. 128/869, 870, 128/874, 875; 602/19, 5

(56) References Cited

U.S. PATENT DOCUMENTS

| | | | | |
|---|---|---|---|---|
| 3,351,053 A | * | 11/1967 | Stuttle | 602/19 |
| 4,202,327 A | | 5/1980 | Glance | |
| 4,245,627 A | * | 1/1981 | Mignard | 602/19 |
| 4,688,558 A | | 8/1987 | Hooper, Jr. et al. | |
| 4,708,130 A | * | 11/1987 | Grudem | 602/19 |
| 5,012,798 A | | 5/1991 | Graf et al. | |
| 5,256,135 A | | 10/1993 | Avihod | |
| 5,267,948 A | * | 12/1993 | Elliott | 602/19 |
| 5,449,338 A | | 9/1995 | Trudell | |
| 5,911,697 A | * | 6/1999 | Biedermann et al. | 602/19 |
| 6,315,746 B1 | | 11/2001 | Garth et al. | |

FOREIGN PATENT DOCUMENTS

DE 3522533 * 1/1987

OTHER PUBLICATIONS

Thomas M. Gavin et al. Principles and Components of Spinal Orthoses 1997 Chapter 8 pp. 155-194, In Atlas of Orthoses and Assistive Devices, 3$^{rd}$ Ed., American Academy of Orthopaedic Surgeons, Mosby-Yearbook, Inc. St Louis, Missouri.

Avinash G. Patwardhan, Ph.D. et al. Orthotic Stabilization of Thoracolumbar Injuries A Biomechanical Analysis of the Jewett Hyperextension Orthosis Mar. 1, 1990 pp. 654-661, Department of Orthopaedics, Loyola University Medical Center, Maywood, Illinois.

Avinash G. Patwardhan, Ph.D. et al. Biomechanics of Implants and Orthoses for Thoracolumbar Injuries May 1993, pp. 203-222, SPINE: State of the Art Reviews, vol. 7, No. 2 Published by Hanley & Belfus, Inc. Philadelphia, Pennsylvania.

S.W. Willner Test Instrument for Predicting the Effect of Rigid Braces in Cases with Low Back Pain 1990, pp. 22-26, Department of Orthopaedics, Malmo General Hospital, Lund University, Malmo, Sweden.

Kevin F. Spratt, Ph.D. et al. Efficacy of Flexion and Extension Treatments Incorporating Braces for Low-Back Pain Patients Retrodisplacement, Spondylolisthesis, or Normal Sagittal Translation Accepted for Publication May 11, 1992, pp. 1839-1849, SPINE: vol. 18, No. 13 1993 L.B. Lippincott Company Spine Diagnostic and Treatment Center, Department of Orthopaedic Surgery, University of Iowa, Hospitals and Clinics Iowa City, Iowa.

Thomas M. Gavin, C.O. et al. Preliminary Results of Orthotic Treatment for Chronic Low Back Pain Jan. 1993, pp. 5/25, 26/6, 7/27, 28/8, 9/29 JPO: Journal of Prosthesis and Orthotics, vol. 5, No. 1, BioConcepts, Inc. Willowbrook, Illinois.

* cited by examiner

Primary Examiner—Michael Anthony Brown
(74) Attorney, Agent, or Firm—Luedeka Neely & Graham PC (57) ABSTRACT An adjustable brace including a substantially rigid shell conforming to a body part of a user and a strap for securing the shell in fitting engagement with the body part, the shell having a substantially rigid central body portion and a pair of opposite and substantially rigid side portions fixedly and adjustably positionable relative to the body portion of the shell, wherein the positions of the side portions may be independently adjusted relative to the body portion of the shell to provide relatively custom fitting of the brace to the user.

9 Claims, 9 Drawing Sheets

SPINAL BRACE

FIELD OF THE INVENTION

This invention relates generally to medical orthoses. More particularly, this invention relates to adjustable braces.

BACKGROUND AND SUMMARY OF THE INVENTION

Conventional braces, and in particular spinal braces, desire improvement, especially in terms of comfort and adjustability. One type of spinal brace is a bi-valve brace having a pair of substantially rigid shells. The shells are typically trimmed using scissors or the like to adjust the size and configuration of the shells to the user. This is inconvenient and limits the usefulness of the shells.

In a preferred embodiment, the invention relates to an adjustable brace including a substantially rigid shell conforming to a body part of a user and a strap for securing the shell in fitting engagement with the body part. The shell has a substantially rigid central body portion and a pair of opposite and substantially rigid side portions fixedly and adjustably positionable relative to the body portion of the shell. The positions of the side portions may be independently adjusted relative to the body portion of the shell to provide relatively custom fitting of the brace to the user.

In another aspect, the invention relates to an adjustable spinal brace. In a preferred embodiment, the spinal brace includes a first substantially rigid shell conforming to a first body part of a user, a second substantially rigid shell conforming to a second body part of the user, and a strap system for securing the shells in fitting engagement with the body parts of the user.

The first shell includes a substantially rigid central body portion and a pair of opposite and substantially rigid side portions fixedly and adjustably positionable relative to the body portion of the shell. The positions of the side portions may be independently adjusted relative to the body portion of the shell to provide relatively custom fitting of the brace to the user.

In yet another aspect, the second shell of the spinal brace is also adjustable and includes a substantially rigid central body portion and a pair of opposite and substantially rigid side portions fixedly and adjustably positionable relative to the body portion of the shell.

BRIEF DESCRIPTION OF THE DRAWINGS

Further features of preferred embodiments of the invention will become apparent by reference to the detailed description of preferred embodiments when considered in conjunction with the figures, which are not to scale, wherein like reference numbers, indicate like elements through the several views, and wherein.

DETAILED DESCRIPTION

Figure 1:
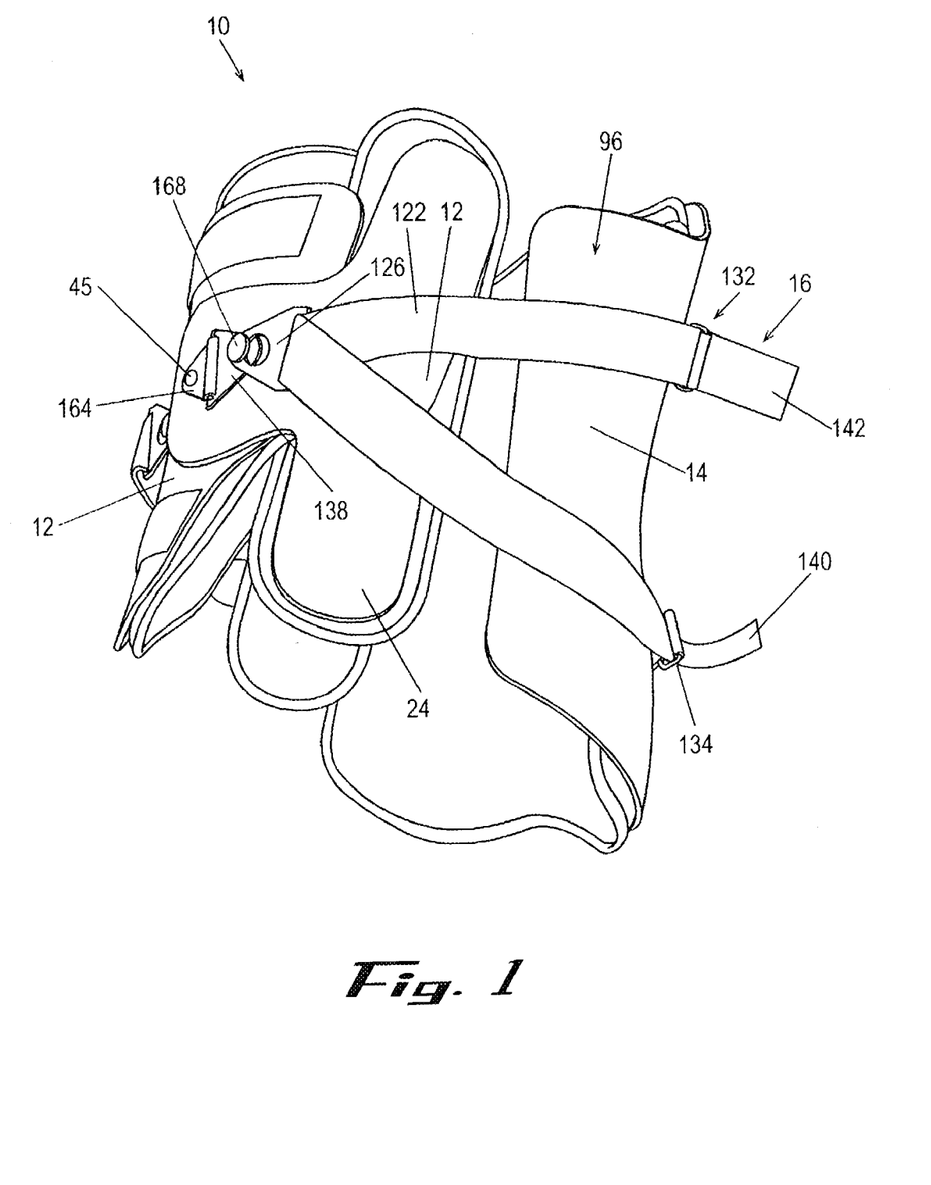
FIG. 1 is a front perspective view of a spinal brace in accordance with a preferred embodiment.

With initial reference to FIG. 1, the invention relates to a spinal brace 10 having a front shell 12, a rear shell 14, and a strap system 16. The depicted brace 10 has shells 12 and 14 particularly configured to serve as a lumbar-sacral orthosis (LSO).

It will be understood, however, that the shells 12 and 14 may be otherwise configured for providing an orthosis suitable for treating other portions of the spine, such as the cervical and thoracic portions. For example, the shells may be configured to provide a thorasic-lumbar-sacral orthosis (TLSO) and a cervical-thorasic-lumbar-sacral orthosis (CTLSO). Likewise, the shells may be configured to impart a particular orientation, such as a flexion, extension, or a neutral orientation to the spine. The brace 10 may also be configured to conform to other parts of the anatomy and used other than as a spinal brace.

The brace 10 advantageously enables convenient and variable adjustment to the configuration of the brace so as to enable it to be quickly and easily fit to a variety of patients and to be repeatedly reconfigured. In a preferred embodiment, this is accomplished by a modular shell member having portions that can be quickly and easily located in a variety of orientations so as to permit the brace to be fit to a user. The preferred configuration described herein utilizes a front shell having a pair of movable, preferably incrementally repositionable, side portions. However, it will be understood that a back shell could alternatively be configured to have movable components. Likewise, for even further adjustability, both the front shell and the rear shell could be configured to have movable side portions.

Front Shell 12

With reference to FIGS. 1–4, the front shell 12 is preferably of molded thermoplastic construction and made of a low density polyethylene material. The thickness of the shell 12 preferably ranges from about ⅛ to about ¼ inch. The front shell 12 is of modular construction and includes a central body portion 20 and opposite side portions 22 and 24 adjustably positionable relative to the body portion 20.

The modular construction of the front shell 12 enables incremental adjustment of the size and configuration of the front shell 12 so that it may be better fit to a user. In addition, the construction of the shell permits for repeated adjustment of the configuration of the front shell 12. This provides improved comfort characteristics and economy.

Figure 2A:
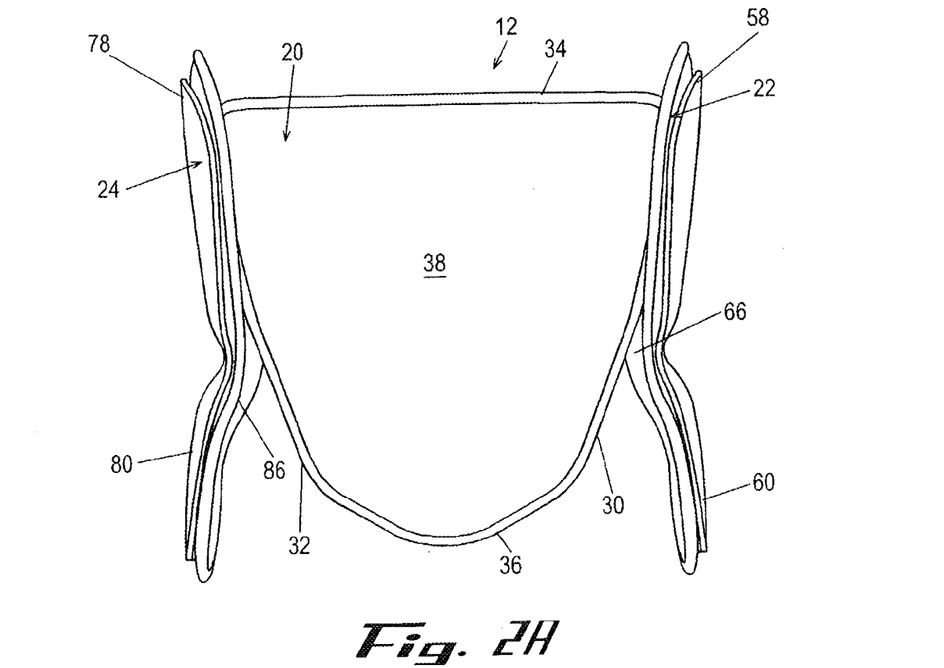
FIGS. 2A and 2B are interior views of a front shell of the brace of FIG. 1.
Figure 2B:
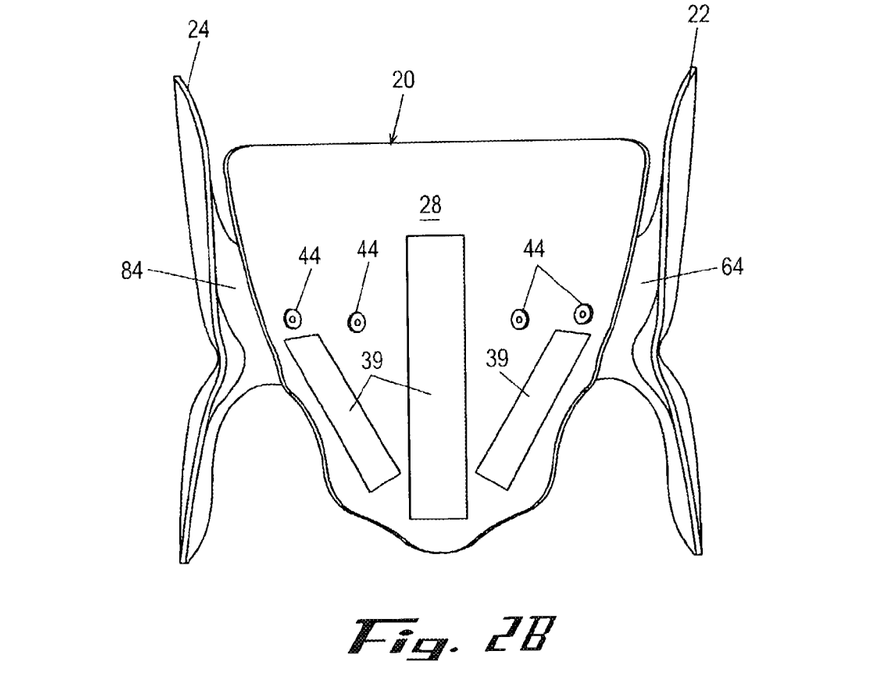

With continued reference to FIGS. 2A–4, the body portion 20 has an exterior surface 26 opposite an interior surface 28, opposite side edges 30 and 32, first edge 34, and second edge 36. A foam liner 38 is preferably attached, as by mating hook and loop material, to the interior surface 28. For example, strips of hook material 39 may be adhesively secured to the interior surface 28, with the hooks thereof matingly engaging the fabric of the liner 38 adjacent the surface 28. FIGS. 2A and 2B are the same, except in FIG. 2B, the foam liners are removed.

A pair of apertures 40a and 40b extend through the body portion 20 at (FIG. 4) a location generally intermediate the first and second edges 34, 36, and adjacent the side edge 30. The apertures 40a and 40b are preferably spaced apart from one another by a distance of from about ½ to about 1 inch.

Another pair of apertures 40c and 40d (FIG. 4) are located through the body portion and spaced from about 1½ to about 2½ inches apart from the pair of apertures 40a and 40b and preferably aligned therewith. In a similar manner, apertures 42a, 42b, 42c, and 42d extend through the shell 12 at a location generally intermediate the first and second edges 34, 36, and adjacent the side edge 32.

The apertures 40a–42d are provided for adjustably mounting the side portions 22 and 24 to the body portion 20, respectively. A fastening device such as a flanged threaded cylinder 44 (FIG. 2B) may be inserted into the apertures 40a–42d, with the flange thereof against the interior surface 28 and the threaded cylinder extending through the apertures 40a–42d for receiving a threaded fastener 45. Additional apertures or spacing schemes may be provided to enable further mounting locations and, hence, adjustment flexibility. For example, the apertures may be located to provide linear and angular adjustment of the positions of the side portions 22 and 24 relative to the body portion 20.

An elongate strip of material 48 having an outer surface configured of a loop or hook material of the type suitable for releasably engaging a hook material or loop material respectively is preferably secured, as by adhesive, substantially laterally across the exterior surface 26 adjacent the first edge 34. Likewise, an elongate strip of material 50 having an outer surface configured of a loop material of the type suitable for releasably engaging a hook material is preferably secured, as by adhesive, substantially laterally across the exterior surface 26 adjacent the second edge 36.

The side portion 22 is substantially T-shaped and has a lateral leg 56, first arm 58, and second arm 60. The side portion 22 has an exterior surface 62 opposite an interior surface 64. A foam liner 66 is preferably attached, as by mating hook and loop material, to the interior surface 64 adjacent the first and second arms 68 and 50, but not the leg 56.

The leg 56 is configured to overlie a portion of the exterior surface 26 of the body portion 20 and includes apertures 68a and 68b located to align with the apertures 40a–40d on the body portion 20. For example, aperture 68a may be positioned to overlie aperture 40a or 40b. When aperture 68a is located to overlie aperture 40a, aperture 68b is thus positioned to overlie aperture 40c. Likewise, aligning the aperture 68a with the aperture 40b renders aperture 68b aligned with aperture 40d. The fasteners 45 may then be used with the aligned apertures to secure the side portions 22 and 24 relative to the body portion 20. The side portion 22 is contoured to conform to the general shape of the abdomen of the user and preferably includes a concavity 70 for placement just above the hips of the user for enhanced fit and comfort.

The side portion 24 is similar in configuration to the side portion 22 and includes a lateral leg 76, first arm 78, and second arm 80. The side portion 24 has an exterior surface 82 opposite an interior surface 84 and foam liner 86. The leg 66 includes apertures 88a and 88b located to adjustably align with the apertures 42a–42d on the body portion 20. The aperture 88a may be aligned with the aperture 42a and 42b, while aperture 88b may be aligned with aperture 42c or 42d. The fasteners 45 may then be used with the aligned apertures to secure the side portions 22 and 24 relative to the body portion 20. The side portion 24 includes a contour 90 corresponding to the contour 70.

Rear Shell 14

Figures 5, 6A:
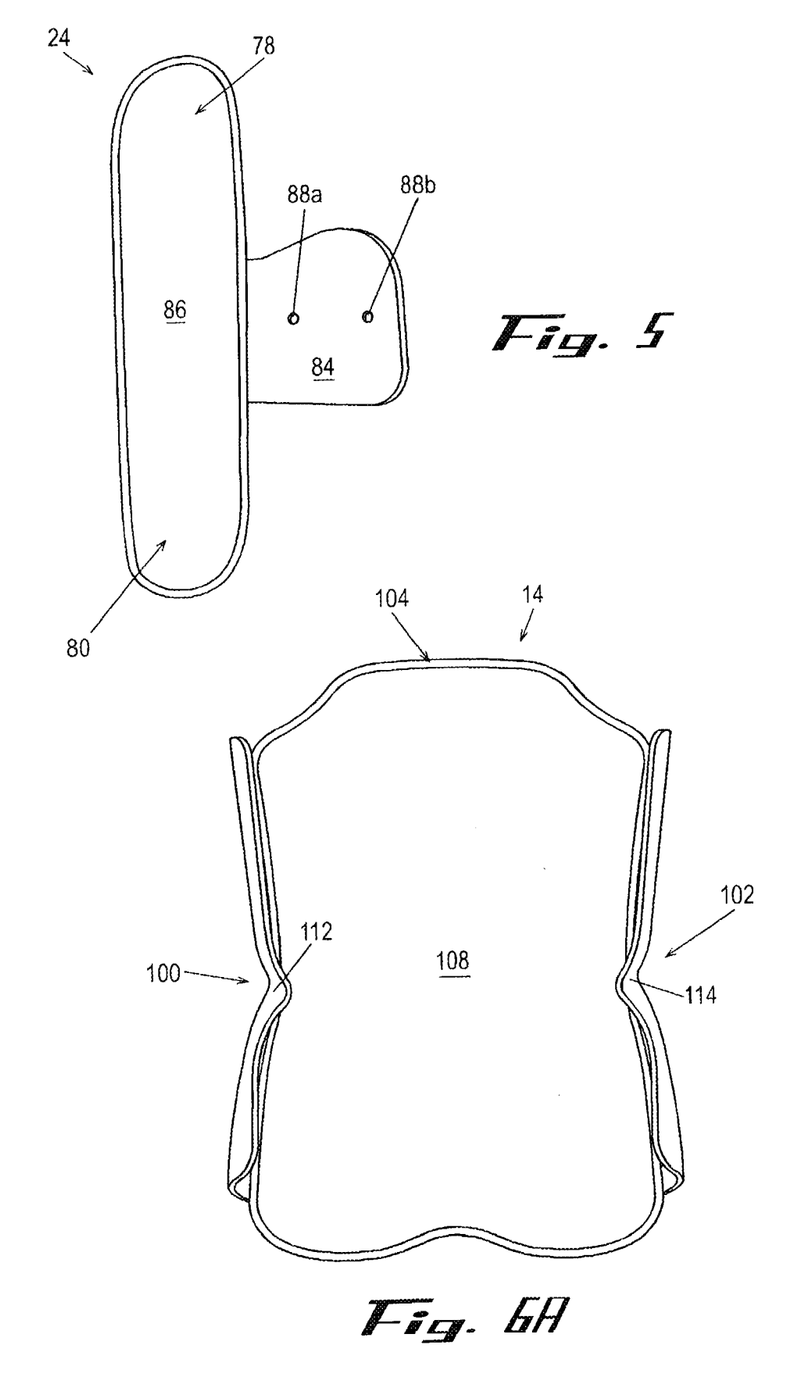
FIG. 5 is a close-up view of one of the components of the shell of FIGS. 2–3.
FIGS. 6A and 6B are interior views of a rear shell of the brace of FIG. 1.
Figure 6B:
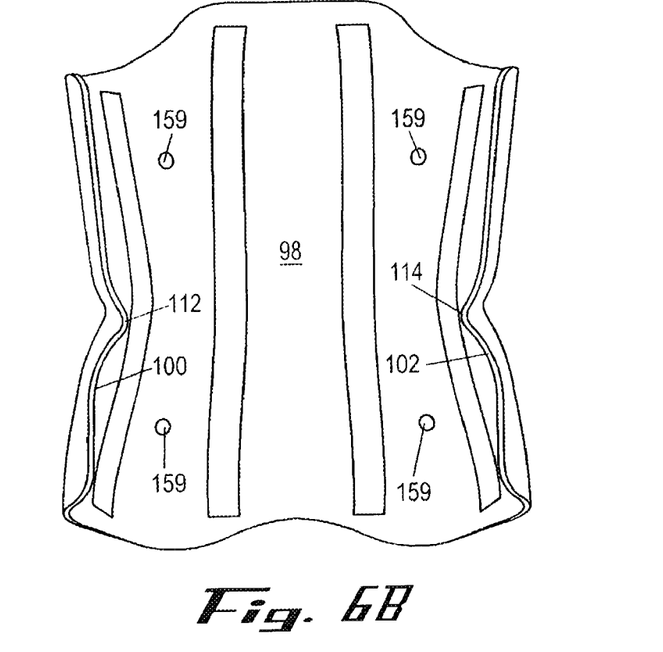
Figure 7:
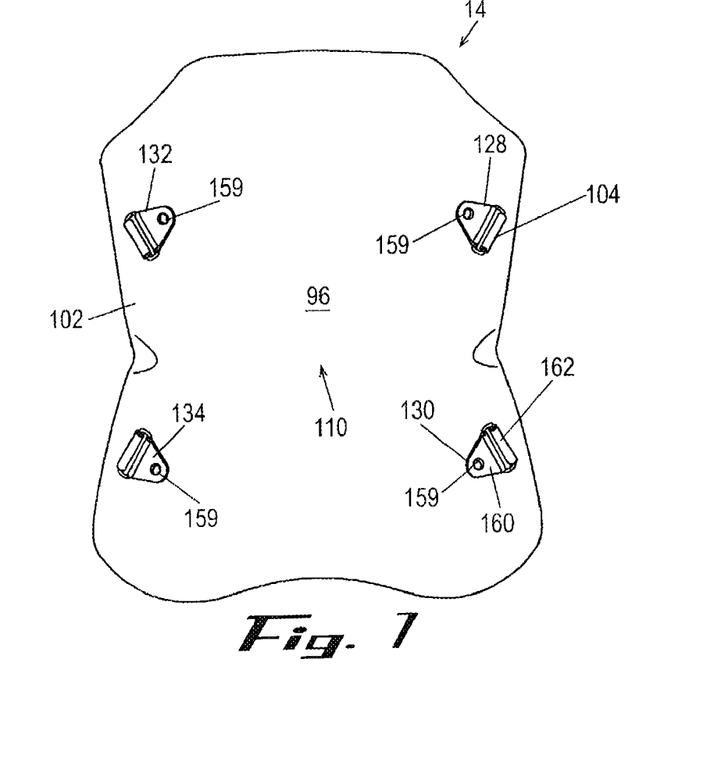
FIG. 7 is an exterior view of the rear shell of the brace of FIG. 1.

With reference to FIGS. 6A, 6B and 7, the rear shell 14 is preferably made of the same material as the front shell 12. The rear shell 14 is configured to partially overlap the front shell 12 when installed on a user and includes an exterior surface 96 opposite an interior surface 98, opposite sides 100 and 102, a first edge 104, a second edge 106, and foam liner 108 adjacent the surface 98. The shells may alternatively be configured so that the front shell 12 partially overlaps the rear shell 14 when installed on a user. FIG. 6B shows the liner 108 removed. The liner 108 may be attached as by strips of hook material 109 adhesively secured to the interior surface 98.

The sides 100 and 102 curve outwardly from a central portion 110 and are configured so that the front shell 12 and the rear shell 14 may be mated when installed on a user. In this regard, the side 100 includes a contour 112 configured to receive the contour 70, and the side 102 includes a contour 114 for the contour 90.

Strap System 16

Figure 8:
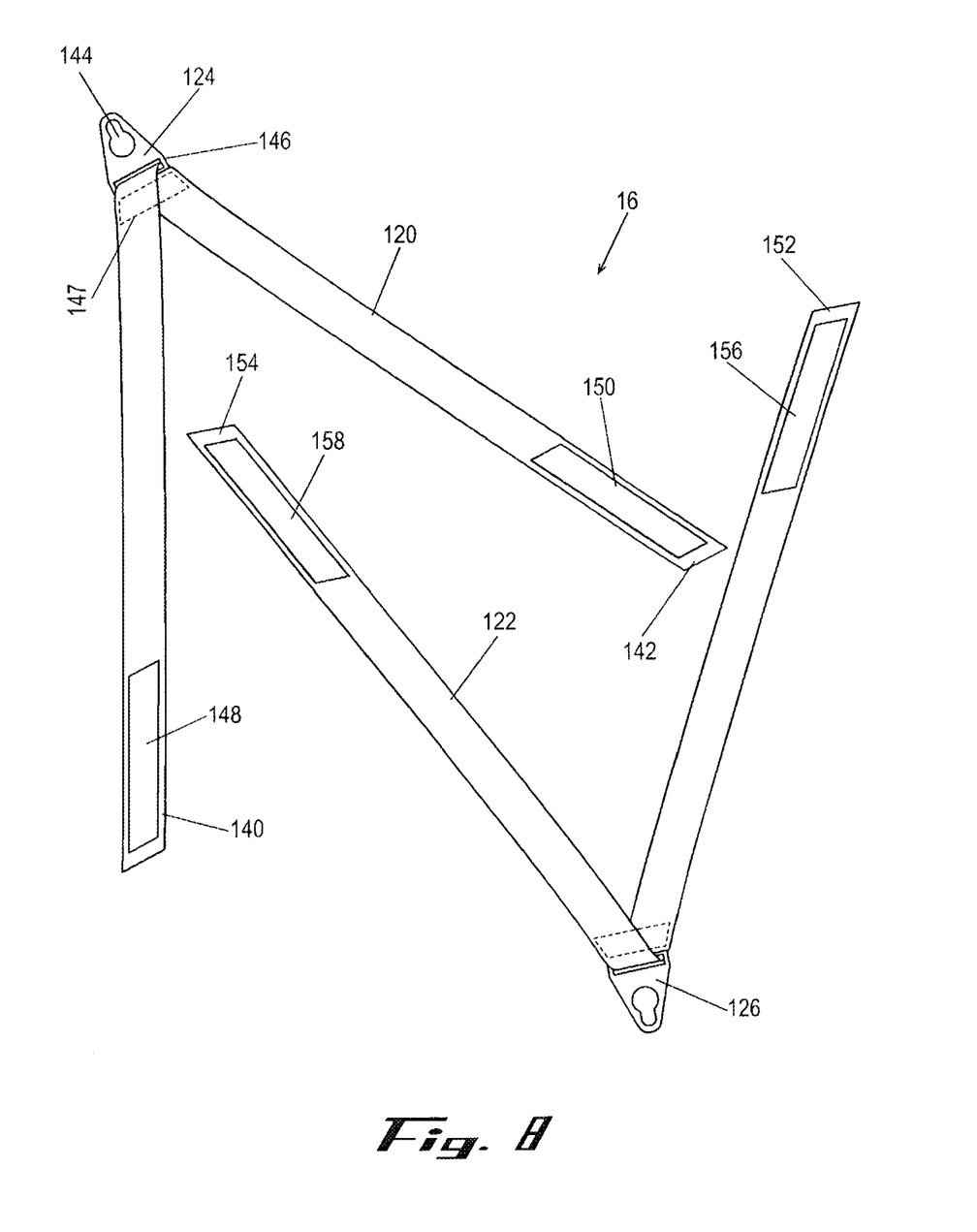
FIG. 8 is a plan view of strap components of the brace of FIG. 1.
Figure 9:
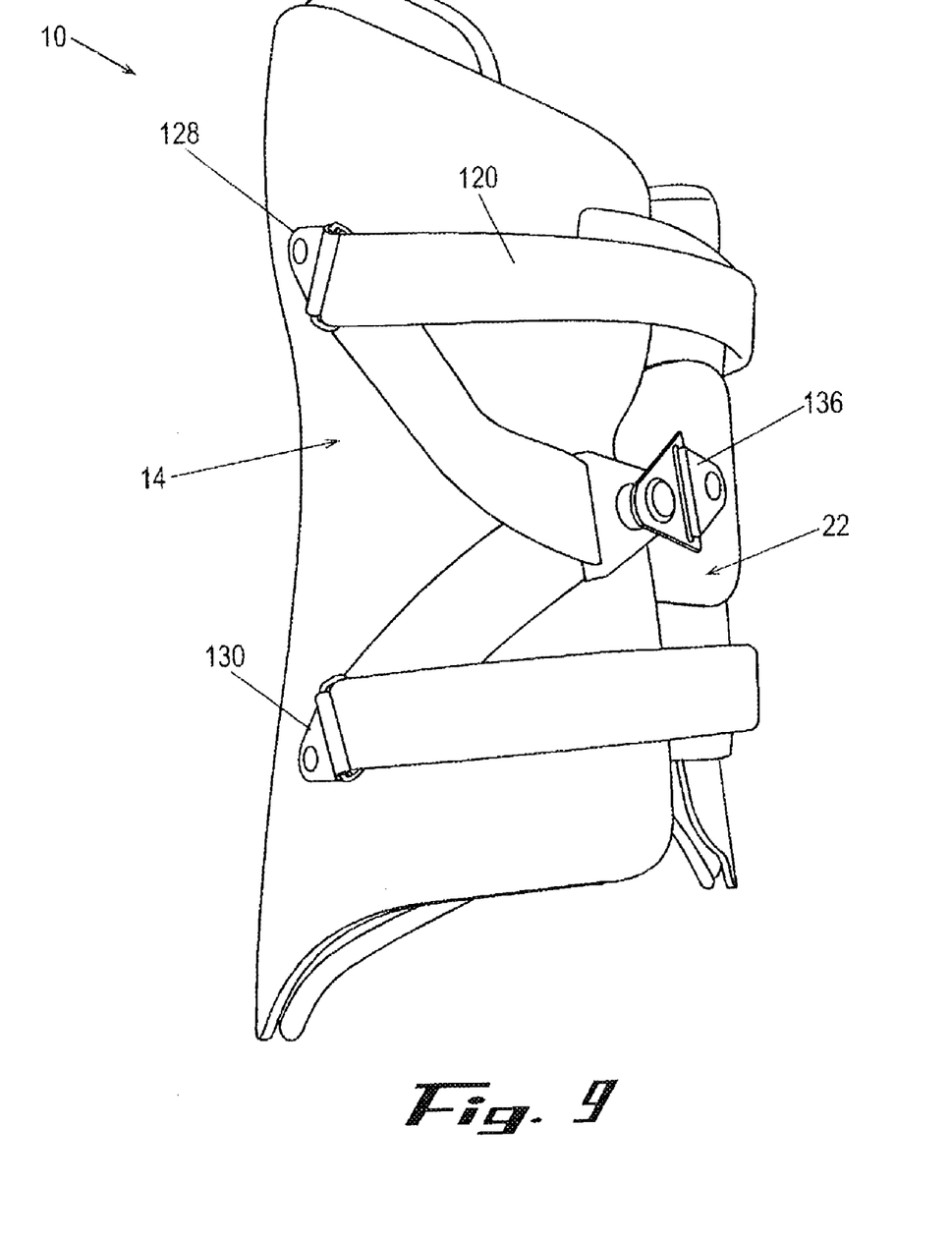
FIG. 9 is a left side view of the brace of FIG. 1 with the straps installed.
Figure 10:
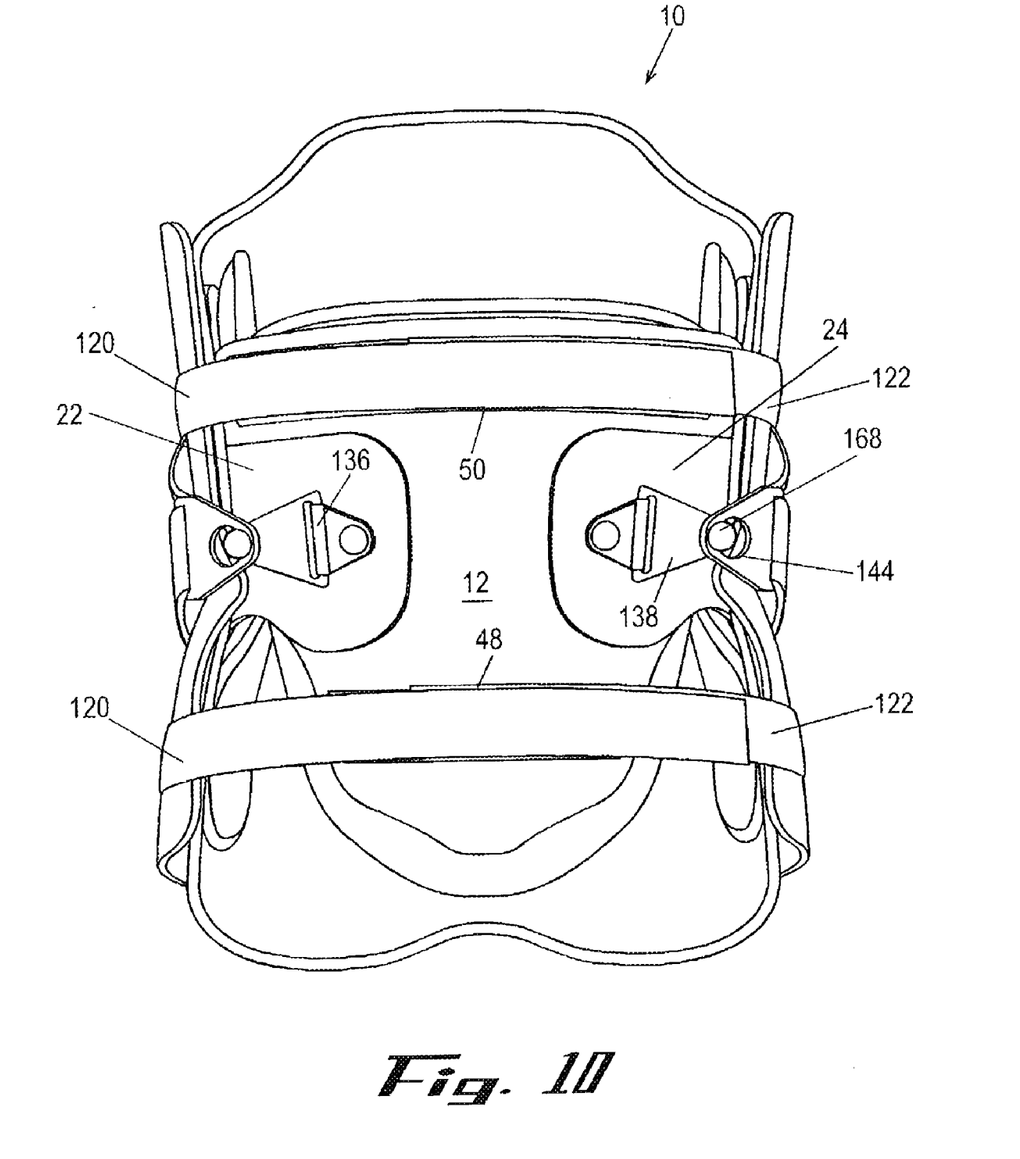
FIG. 10 is a frontal view of the brace of FIG. 1 with the straps installed.

With reference to FIGS. 8–10, the strap system 16 includes a pair of straps 120 and 122, and a pair of buckles 124 and 126 fixedly secured on the straps 120 and 122. Slides 128, 130, 132, and 134 (FIG. 7) are attached to the exterior surface 96 of the rear shell 14, and latch members 136 and 138 are attached to the side portions 22 and 24.

The strap 120 preferably has a length ranging of from about 38 to about 48 inches and includes opposite ends 140 and 142. The buckle 124 is preferably of one-piece plastic construction and includes a latching aperture 144 and a mounting slit 146. Returning to FIG. 8, the strap 120 is passed through the slit 146 and the buckle 124 positioned at about the midpoint of the strap 120. The strap 120 is folded about itself and secured, as by stitches 147, to form the strap in a generally A-shape, with the buckle 124 fixedly located at the apex. A hook material 148 is preferably provided on the strap 120 adjacent the end 140 and a hook material 150 is preferably provided on the strap 120 adjacent the end 142. The strap 122 is preferably identical to the strap 120 and is identically configured with regard to the buckle 126 and includes ends 152 and 154 and hook material 156 and 158.

The slides 128–134 are configured for receiving and slidably retaining the straps and are mountable to the shell 14 as by fasteners such as rivets 159 or the like. As will be seen, each slide 128–134 includes a mounting base 160 and an elongate loop 162 pivotally mounted to the base 160 and configured for passage of the straps 120 or 122 there through.

Figure 3:
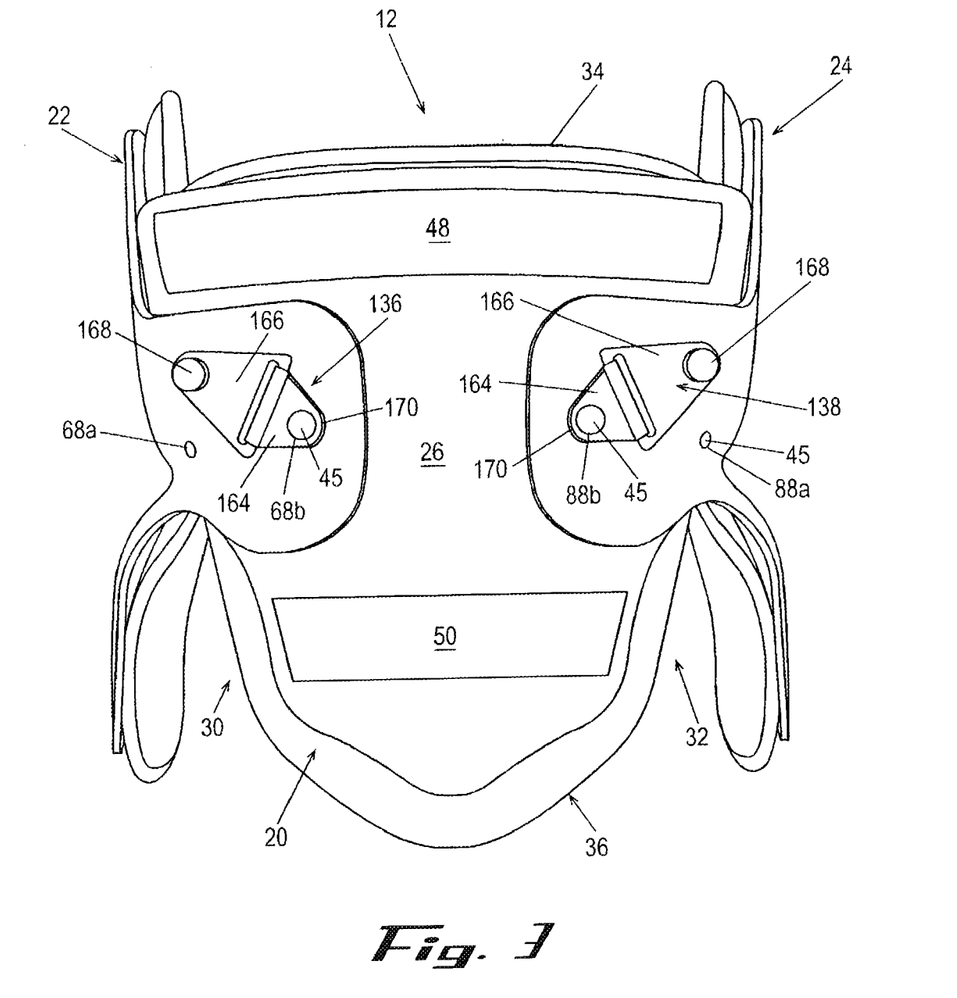
FIG. 3 is an exterior view of the front shell of the brace of FIG. 1.
Figure 4:
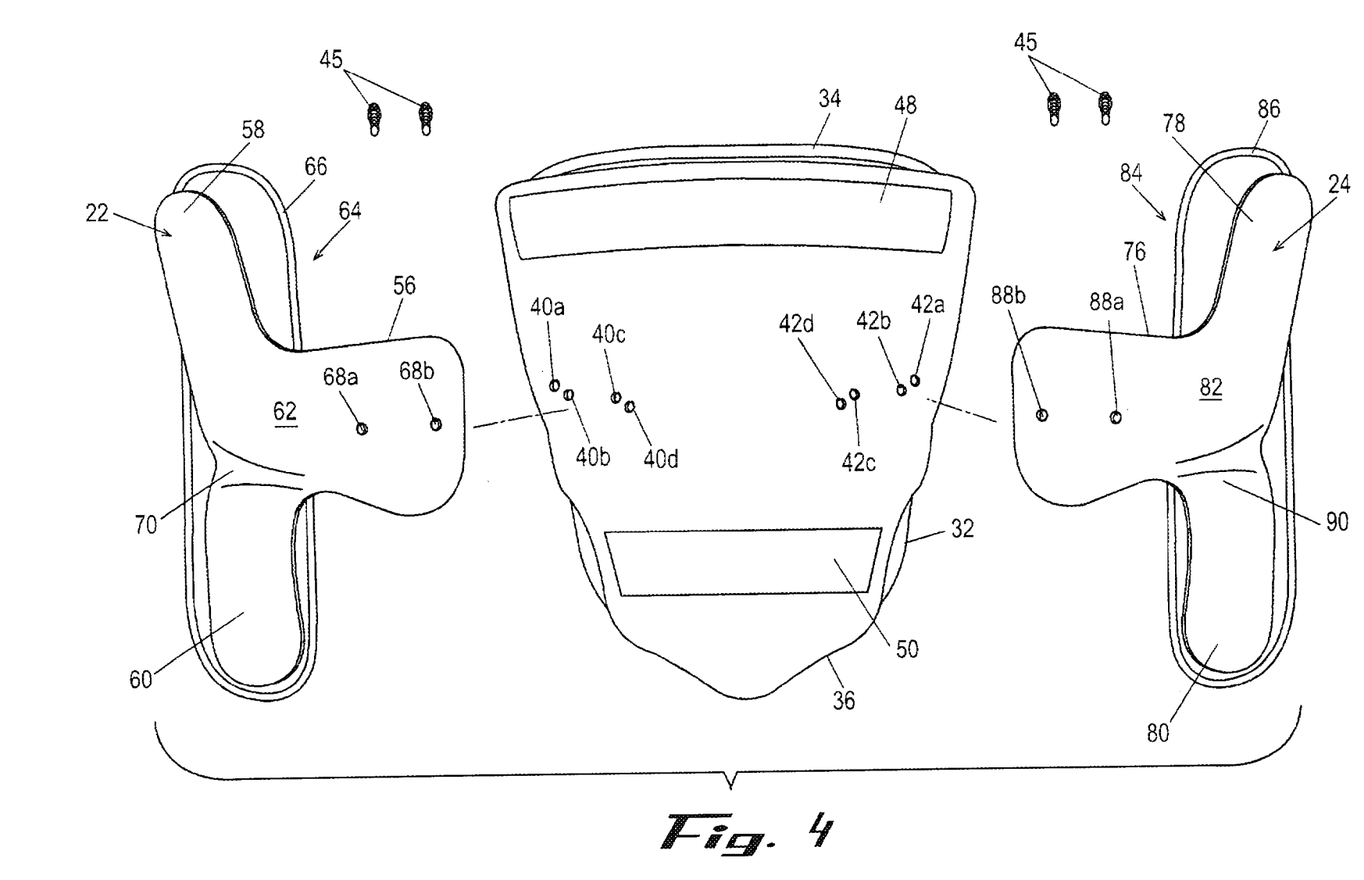
FIG. 4 is an exploded view of the components of the front shell of FIGS. 2 and 3.

As best seen in FIG. 3, the latch members 136 and 138 each include a base 164 for mounting to the shell 12 and a latch 166 pivotally mounted to the base 164. The latch 166 is configured for releasably engaging the latching aperture of a buckle, such as latching aperture 144 of buckle 124, and preferably includes a mushroom-shaped projection 168 for releasably engaging the latching apertures 144 of the buckles.

The base 164 preferably includes an aperture 170 for passage of a fastener 45. Each of the latch members may be mounted adjacent one of the apertures 68a–68b or 88a–88b by aligning the aperture 170 of the base 164 with the aperture 68a–68b or 88a–88b and passing the fastener 45 there through.

Installation and Use

Returning to FIGS. 1, 9 and 10, the brace 10 is installed around the trunk of a user by placing the front shell 12 adjacent the front of the user and the rear shell adjacent the spine of the user, with the sides 100 and 102 of the rear shell 14 overlapping the sides portions 22 and 24 of the front shell 12. As mentioned previously, the position of the side portions 22 and 24 may be easily and quickly adjusted relative to the body portion 20 to provide relatively custom fitting of the brace 10 to the user.

As seen in FIG. 1, the buckles of the straps, such as buckle 124 of the strap 122, is secured to the latch members, such as latch member 138, as by engaging the latching aperture around the projection 168. Also, the straps are passed through the slides, as by passing ends 140 and 142 through the slides 132 and 134, as shown in FIG. 1. Next, the shells 12 and 14 are urged toward one another as desired by pulling on the ends of each of the straps to place the ends adjacent the strips of loop material 48 and 50. The hook material associated with the our ends of the straps, such as hook material 148 and 150, is then matingly engaged with the loop material 48 and 50. As will be appreciated, the ends of the straps may be overlapped, as the exterior surfaces of the strap provide a loop material engageable with the hook material. As will be appreciated, the location of the hook and loop material may be interchanged and other releasable fastening devices, such as snaps, buckles, and the like may be used.

If adjustment of the fit of the brace is desired, the side portions 22 and 24 may be readily and repeatedly repositoned relative to the body portion 20. Also, if desired, the rear shell 14 may be configured in the manner similar to the front shell 12 and have the sides 100 and 102 as separate pieces which can be attached in an adjustable manner in the same manner as the side portions 22 and 24.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. An adjustable brace, comprising a substantially rigid shell generally conforming to a body part of a user and a strap for securing the shell in fitting engagement with the body part of the user, the shell having a substantially rigid central body portion and a pair of opposite and substantially rigid and substantially T-shaped side portions each having a lateral leg and a pair of oppositely extending arms, with the leg being configured to connect to and to be fixedly and adjustably positionable relative to the body portion of the shell to enable linear and angular adjustment of the positions of the side portions relative to the body portion of the shell to provide relatively custom fitting of the brace to the user.

2. The brace of claim 1, wherein the brace is a spinal brace.

3. The brace of claim 1, wherein the brace further includes a plurality of fasteners, the body portion of the shell includes a plurality of apertures extending therethrough, and each of the legs of the side portions of the shell includes a plurality of apertures extending therethrough, wherein each of the apertures of the legs of the side portions are selectively alignable with at least one of the apertures of the body portion of the shell and each of the fasteners is insertable within aligned ones of the apertures of the body portion of the shell and the legs of the side portions to secure the legs of the side portions to the body portion of the shell.

4. An adjustable spinal brace, comprising a first substantially rigid shell generally conforming to a first body part on a torso of a user, a second substantially rigid shell generally conforming to a second body on the torso part of the user, and a strap system for securing the shells in fitting engagement with the body parts of the user, wherein the first shell includes a substantially rigid central body portion and first and second substantially and substantially T-shaped rigid side portions each having a lateral leg and a pair of oppositely extending arms, with the leg being configured to connect to and to be fixedly and adjustably positionable relative to the body portion of the first shell, on opposite sides thereof to enable linear and angular adjustment of the positions of the side portions relative to the body portion of the shell to provide relatively custom fitting of the brace to the user.

5. The brace of claim 4, wherein the second shell includes a substantially rigid central body portion and third and fourth substantially rigid side portions fixedly and adjustably positionable relative to the body portion of the second shell on opposite sides thereof.

6. The brace of claim 4, wherein the first and second shells are configured so that one of the shells partially overlap the other one of the shells when installed on a user.

7. The brace of claim 4, wherein the strap system includes a first strap and a first buckle secured to the first strap, a second strap and a second buckle secured to the second strap, a plurality of slides securable to the second shell for receiving the straps, a first latch member securable to one of the first and second side portions of the first shell, and a second latch member securable to the other of one of the first and second side portions of the first shell.

8. An adjustable spinal brace, comprising a first substantially rigid shell generally conforming to a first body part on a torso of a user, a second substantially rigid shell generally conforming to a second body part on the torso part of the user, the second shell including a substantially rigid central body portion and third and fourth substantially rigid side portions fixedly and adjustably positionable relative to the central body portion on opposite sides thereof, and a strap system for securing the shells in fitting engagement with the body parts of the user, wherein the first shell includes a substantially rigid central body portion and first and second substantially rigid side portions fixedly and adjustably positionable relative to the body portion of the first shell, on opposite sides thereof and wherein the positions of the first and second side portions may be independently adjusted relative to the body portion of the shell to provide relatively custom fitting of the brace to the user.

9. An adjustable spinal brace, comprising a first substantially rigid shell generally conforming to a first body part on a torso of a user, a second substantially rigid shell generally conforming to a second body on the torso part of the user, and a strap system for securing the shells in fitting engagement with the body parts of the user, wherein the first shell includes a substantially rigid central body portion and first and second substantially rigid side portions fixedly and adjustably positionable relative to the body portion of the first shell, on opposite sides thereof and wherein the positions of the first and second side portions may be independently adjusted relative to the body portion of the shell to provide relatively custom fitting of the brace to the user, and wherein the strap system includes a first strap and a first buckle secured to the first strap, a second strap and a second buckle secured to the second strap, a plurality of slides securable to the second shell for receiving the straps, a first latch member securable to one of the first and second side portions of the first shell, and a second latch member securable to the other of one of the first and second side portions of the first shell.

* * * * *